(12) United States Patent
Liu et al.

(10) Patent No.: US 11,235,283 B2
(45) Date of Patent: Feb. 1, 2022

(54) IONIC LIQUID AND FORWARD OSMOSIS PROCESS EMPLOYING THE SAME

(71) Applicant: INDUSTRIAL TECHNOLOGY RESEARCH INSTITUTE, Hsinchu (TW)

(72) Inventors: Po-I Liu, Kaohsiung (TW); Hsin Shao, Zhubei (TW); Min-Chao Chang, Hsinchu (TW); Yi-Chun Chen, Hsinchu (TW); Chiung-Hui Huang, Tainan (TW); Chia-Hua Ho, Miaoli (TW); David Chiuni Wang, Hsinchu (TW); Ren-Yang Horng, Hsinchu (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 86 days.

(21) Appl. No.: 16/729,910

(22) Filed: Dec. 30, 2019

(65) Prior Publication Data
US 2021/0197122 A1    Jul. 1, 2021

(51) Int. Cl.
*B01D 61/00* (2006.01)
*C02F 1/44* (2006.01)
(Continued)

(52) U.S. Cl.
CPC ............ *B01D 61/005* (2013.01); *C02F 1/445* (2013.01); *C02F 1/68* (2013.01); *C07C 47/19* (2013.01);
(Continued)

(58) Field of Classification Search
CPC .............. B01D 61/005; B01D 11/0484; B01D 11/0488; B01D 11/0492; B01D 61/002;
(Continued)

(56) References Cited

U.S. PATENT DOCUMENTS 3,673,110 A * 6/1972 Edwards ............... D06M 15/61
510/513
8,609,572 B2 * 12/2013 Earl ..................... B01J 31/0237
502/150
(Continued)

FOREIGN PATENT DOCUMENTS

CN          1698929 A      11/2005
CN        102659834 A       9/2012
(Continued)

OTHER PUBLICATIONS

Supritam Dutta et al, "Prospect of ionic liquids and deep eutectic solvents as new generation draw solution in forward osmosis process", Journal of Water Process Engineering, Published 2018, vol. 1, pp. 163-176 (Year: 2018).*
(Continued)

*Primary Examiner* — Joseph W Drodge
(74) *Attorney, Agent, or Firm* — Birch, Stewart, Kolasch & Birch, LLP

(57) ABSTRACT

An ionic liquid and a forward osmosis process employing the same are provided. The ionic liquid has a structure represented by Formula (I)

$$AB_n \qquad \text{Formula (I)},$$

wherein A is (Continued)

-continued

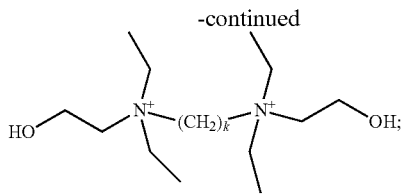

n is 1 or 2; m is 0, or an integer from 1 to 7; $R^1$ and $R^2$ are independently methyl or ethyl; k is an integer from 3 to 8; B is

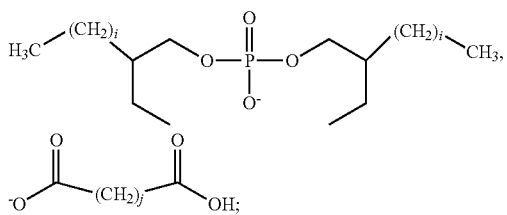

i is independently 1, 2, or 3; and j is 5, 6, or 7. The forward osmosis process employing the ionic liquid is used to desalinate a brine via a forward osmosis (FO) model.

19 Claims, 4 Drawing Sheets

(51) Int. Cl.
   *C02F 1/68* (2006.01)
   *C07C 47/19* (2006.01)
(52) U.S. Cl.
   CPC ...... *B01D 2311/10* (2013.01); *C02F 2209/02* (2013.01); *C02F 2209/03* (2013.01); *C02F 2305/00* (2013.01)
(58) Field of Classification Search
   CPC ............ B01D 2252/30; B01D 2311/06; B01D 2311/10; B01D 2311/103; B01D 2311/106; B01D 2311/12; B01D 2311/26; B01D 2311/2626; C02F 1/445; C02F 1/68; C02F 2305/00; C02F 2209/02; C02F 2209/03; C02F 1/02; C02F 1/26; C02F 2103/08; C07C 47/19; C07C 47/195; C07C 47/20; C07C 57/00; C07C 57/52; C07F 9/02
   See application file for complete search history.

(56) References Cited

U.S. PATENT DOCUMENTS

| | | | |
|---|---|---|---|
| 9,399,194 B2 | 7/2016 | Wilson et al. | |
| 9,492,789 B2 | 11/2016 | Kim et al. | |
| 9,550,728 B2 | 1/2017 | Lee et al. | |
| 10,016,725 B2 | 7/2018 | LiU et al. | |
| 10,195,543 B2 | 2/2019 | Wilson et al. | |
| 2012/0190905 A1* | 7/2012 | Gorke | B01D 53/228 585/818 |
| 2013/0105377 A1* | 5/2013 | Jessop | C02F 1/445 210/203 |
| 2013/0240444 A1 | 9/2013 | Jung et al. | |
| 2013/0256228 A1* | 10/2013 | Bharwada | C02F 1/445 210/644 |
| 2014/0076810 A1* | 3/2014 | Jessop | C08F 8/32 210/638 |
| 2014/0217026 A1 | 8/2014 | Han et al. | |
| 2015/0232777 A1* | 8/2015 | Qu | C10M 137/12 508/369 |
| 2016/0074810 A1 | 3/2016 | Hu et al. | |
| 2016/0082391 A1 | 3/2016 | Hu et al. | |
| 2017/0044030 A1* | 2/2017 | Alamaru | B01D 71/56 |
| 2017/0259210 A1* | 9/2017 | Kanemaru | C02F 1/445 |
| 2018/0008933 A1* | 1/2018 | Hu | B01D 61/005 |
| 2018/0015414 A1* | 1/2018 | Hu | B01D 61/027 |
| 2018/0346938 A1* | 12/2018 | Xu | C12P 7/10 |
| 2019/0003465 A1* | 1/2019 | Hu | B01D 61/44 |
| 2019/0136281 A1* | 5/2019 | Gladden | C12P 19/14 |
| 2020/0030716 A1* | 1/2020 | Hatton | B01D 57/00 |
| 2021/0197123 A1* | 7/2021 | Chen | C02F 1/445 |
| 2021/0292196 A1* | 9/2021 | Hatton | C25C 3/00 |

FOREIGN PATENT DOCUMENTS

| | | |
|---|---|---|
| CN | 103204788 B | 7/2013 |
| CN | 102642894 A | 8/2016 |
| CN | 103319723 B | 12/2016 |
| TW | I586681 B | 6/2017 |
| TW | I658045 A | 5/2019 |
| WO | WO 2011/097727 A1 | 8/2011 |
| WO | WO 2014/175833 A1 | 10/2014 |
| WO | WO 2014/175834 A1 | 10/2014 |
| WO | WO 2015/147749 A1 | 10/2015 |
| WO | WO 2016/027280 A3 | 2/2016 |
| WO | WO 2018/067019 A3 | 4/2018 |

OTHER PUBLICATIONS

Taiwanese Office Action and Search Report for Taiwanese Application No. 108148332 dated Oct. 8, 2020.
Abdul Mutalib et al., "Ecotoxicity of Ionic Liquids Towards Vibrio fischeri: Experimental and QSAR Studies", Ecotoxicity of Ionic Liquids Towards Vibrio fischeri: Experimental and QSAR Studies, pp. 430-449, 23 pages total. (published 2017).
Bai et al., "Highly water soluble and recovered dextran coated Fe3O4 magnetic nanoparticles for brackish water desalination", Separation and Purification Technology, vol. 81, 2011, 392-399.
Cai et al., "Energy-efficient desalination by forward osmosis using responsive ionic liquid draw solutes", Environmental Science Water Research & Technology, vol. 1, 2015, pp. 341-347.
E Silva et al., "Sustainable design for environment-friendly mono and dicationic cholinium-based ionic liquids", Ecotoxicology and Environmental Safety, vol. 108, 2014, pp. 302-310.
Li et al., "Stimuli-responsive polymer hydrogels as a new class of draw agent for forward osmosis desalination", Chem. Commun., vol. 47, 2011, pp. 1710-1712.
Liu et al., "The physical properties of aqueous solutions of the ionic liquid [BMIM][BF$_4$]", Journal of Solution Chemistry, vol. 35, 2006, pp. 1337-1346.
Mondal et al. "Deep eutectic solvents as new class of draw agent to enrich low abundant DNA and proteins using forward osmosis", RSC Advances, 2015, pp. 1-7.
Nockemann et al. Temperature-Driven Mixing-Demixing Behavior of Binary Mixtures of the Ionic Liquid Choline Bis(trifluoromethylsulfonyl)imide and Water, J. Phys. Chem. B, vol. 113, 2009, 1429-1437.
Razmjou et al., "Effect of particle size on the performance of forward osmosis desalination by stimuli-responsive polymer hydrogels as a draw agent", Elsevier, Chemical Engineering Journal, vol. 215-216, 2013, pp. 913-920.
Ventura et al., "Toxicity assessment of various ionic liquid families towards *Vibrio fischeri* marine bacteria", Ecotoxicology and Environmental Safety, vol. 76, 2012, pp. 162-168.

* cited by examiner

IONIC LIQUID AND FORWARD OSMOSIS PROCESS EMPLOYING THE SAME

TECHNICAL FIELD

The disclosure relates to an ionic liquid and forward osmosis process employing the same.

BACKGROUND

The technical principle of forward osmosis (FO) desalination process utilizes an osmotic pressure difference (between two solutions/solutes in two parts separated by a semi-permeable membrane) as a driving force. Water in a feed part with a lower osmotic pressure will permeate through a semi-permeable membrane into a draw solution part with a higher osmotic pressure. The mixture liquid of the water (permeating through the semi-permeable membrane) and the draw solution can be separated or concentrated to separate the water and the draw solution, thereby recycling the draw solution and producing pure water. In water treatment, the forward osmosis process has advantages such as low energy consumption and low membrane fouling ratio, which may largely enhance the function stability and cost effectiveness.

The draw solution should have the properties of high osmotic pressure, hydrophilicity, and being easily separated from water, in which the separation of the draw solution and the water (through the semi-permeable membrane) and the recycling of the draw solution are critical factors of energy consumption in the forward osmosis process. Currently there are a lot of draw solutions that have high osmotic pressure, but they are not suitable for practical applications due to problems of high toxicity and high energy consumption.

Therefore, a novel draw solution for the forward osmosis desalination process is still called for to solve the problem described above.

SUMMARY

According to embodiments of the disclosure, the disclosure provides an ionic liquid. The ionic liquid can have a structure represented by Formula (I):

$$AB_n \qquad \text{Formula (I)},$$

wherein A is

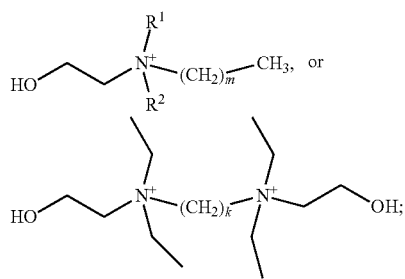

n is 1 or 2; $R^1$ and $R^2$ are independently methyl or ethyl; m is 0, or an integer from 1 to 7; k is an integer from 3 to 8; B is

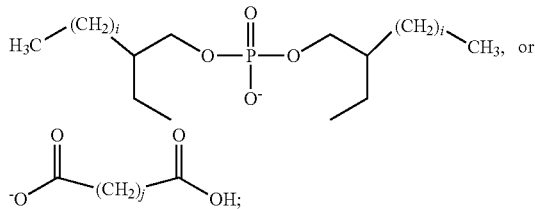

i is independently 1, 2, or 3; and j is 5, 6, or 7.

According to embodiments of the disclosure, the disclosure provides a forward osmosis process. The forward osmosis process includes following steps. A semi-permeable membrane is provided, wherein a draw solution tank is separated from a feed water tank by the semi-permeable membrane. A draw solution is introduced into the draw solution tank, wherein the draw solution includes the ionic liquid of the disclosure. A brine is introduced into a feed water tank, and the osmotic pressure of the brine is lower than the osmotic pressure of the ionic liquid so that the water of the brine permeates through the semi-permeable membrane into the draw solution to obtain a diluted draw solution. The diluted draw solution is extracted from the draw solution tank. The diluted draw solution is subjected to a temperature control treatment so that the diluted draw solution is subsequently separated into a water phase and an ionic liquid phase.

A detailed description is given in the following embodiments with reference to the accompanying drawings.

DETAILED DESCRIPTION

Figure 1:
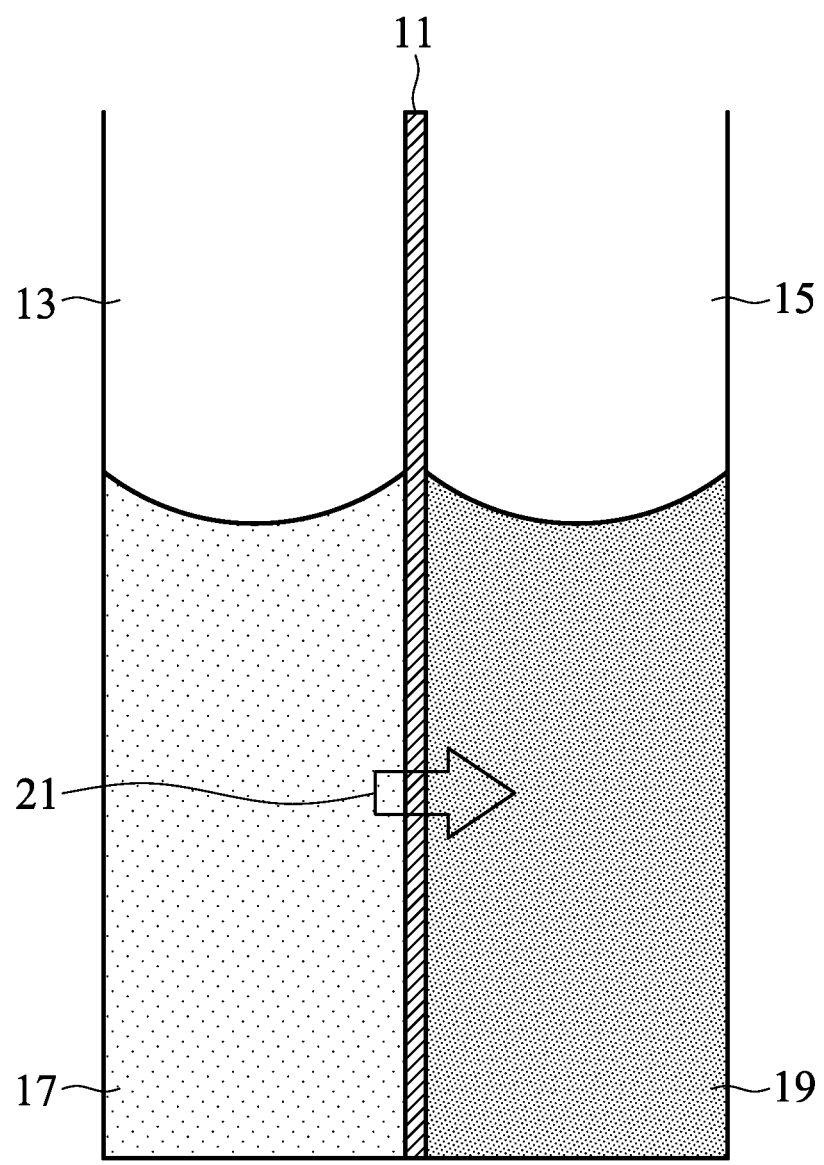
FIG. 1 is a schematic diagram of the forward osmosis process according to an embodiment of the disclosure.

The ionic liquid and forward osmosis process employing the same of the disclosure are described in detail in the following description. In the following detailed description, for purposes of explanation, numerous specific details and embodiments are set forth in order to provide a thorough understanding of the present disclosure. The specific elements and configurations described in the following detailed description are set forth in order to clearly describe the present disclosure. It will be apparent, however, that the exemplary embodiments set forth herein are used merely for the purpose of illustration, and the inventive concept may be embodied in various forms without being limited to those exemplary embodiments.

According to embodiments of the disclosure, the disclosure provides an ionic liquid. The ionic liquid of the disclosure is a choline-based ionic liquid.

According to embodiments of the disclosure, the ionic liquid of the disclosure consists of an anionic portion (B) and an cation portion (A) and can have a structure represented by Formula (I):

AB$_n$    Formula (I)

, wherein A is

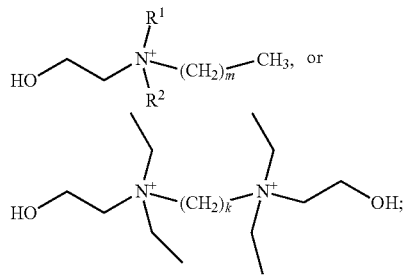

n is 1 or 2; m is 0, 1, 2, 3, 4, 5, 6, or 7; $R^1$ and $R^2$ are independently methyl or ethyl; k is 3, 4, 5, 6, 7, or 8; B is

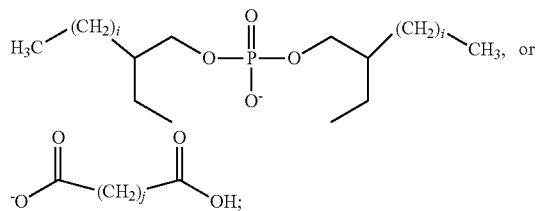

i is independently 1, 2, or 3; and j is 5, 6, or 7. Since the ionic liquid of the disclosure employs the specific anionic portion (B) in cooperation with the specific cation portion (A), the ionic liquid not only exhibits the characteristics of ionic liquid (such as high solubility, extremely low vapor pressure, high thermal stability and electrochemical stability), but also has advantages of relatively high molecular weight, high hydrophilicity, biocompatibility, low biological toxicity, low manufacturing cost and high environmental adaptability. Therefore, the ionic liquid can be widely applied in organic synthesis, isolation, purification, or electrochemical fields.

According to embodiments of the disclosure, the ionic liquid of the disclosure can have a structure represented by AB, wherein A can be

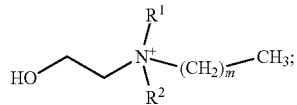

B can be

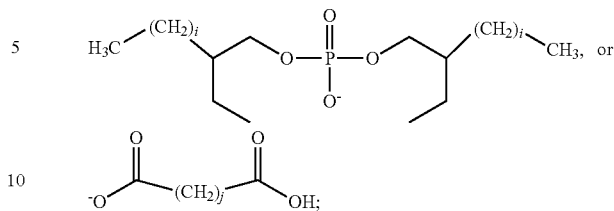

m is 0, 1, 2, 3, 4, 5, 6, or 7; $R^1$ and $R^2$ are independently methyl or ethyl; i is independently 1, 2, or 3; and j is 5, 6, or 7.

According to embodiments of the disclosure, the ionic liquid of the disclosure can have a structure represented by AB$_2$, wherein A can be

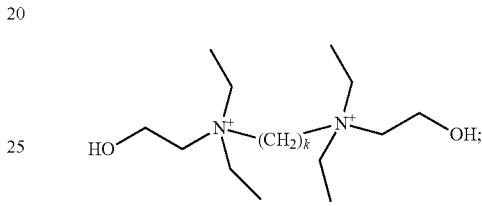

B can be

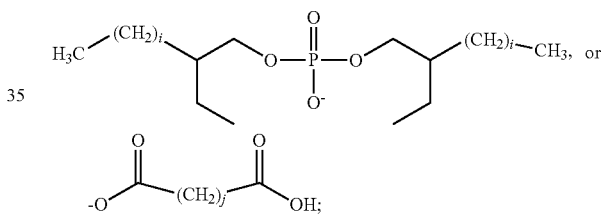

k is 3, 4, 5, 6, 7, or 8; i is independently 1, 2, or 3; and j is 5, 6, or 7.

According to embodiments of the disclosure, the disclosure provides a draw solution can be used in the forward osmosis process. The draw solution can consist of the ionic liquid of the disclosure. In addition, according to some embodiments of the disclosure, the draw solution can include water and the ionic liquid of the disclosure, wherein the amount of ionic liquid in the draw solution can be 5 wt % to 95 wt % (such as 10 wt %, 15 wt %, 20 wt %, 25 wt %, 30 wt %, 35 wt %, 40 wt %, 45 wt %, 50 wt %, 55 wt %, 60 wt %, 65 wt %, 70 wt %, 75 wt %, 80 wt %, 85 wt %, 90 wt %, or 95 wt %), based on the weight of the draw solution. According to embodiments of the disclosure, the amount of ionic liquid in the draw solution can be 10 wt % to 70 wt %. It should be noted, since the draw solution of the disclosure can be a forward osmosis draw solution, the concentration of the draw solution is not limited in a specific range. The forward osmosis draw solution would work when the osmotic pressure of draw solution is greater than the osmotic pressure of brine at the specific concentration. In general, the extraction efficiency is better when the osmotic pressure difference between the draw solution and the raw material liquid is larger. Therefore, the aqueous solution, having a high concentration of ionic liquid and serving as the draw solution, exhibits a superior extraction efficiency.

However, in terms of the cost, the requirement of the forward osmosis draw solution is that the osmotic pressure of the forward osmosis draw solution is greater than the osmotic pressure of the raw material liquid under the specific concentration of the forward osmosis draw solution. Since the ionic liquid of the disclosure is liquid phase solution, the ionic liquid (even in the concentration in 100 wt %) (i.e. pure ionic liquid) can directly serve as a draw solution. However, according to the osmotic pressure of the brine, an aqueous solution with various ionic liquid concentration can be optionally used as the draw solution. The ionic liquid of the disclosure has a relatively high molecular weight but the viscosity thereof is low. Therefore, a solution with relatively high ionic liquid concentration can be prepared and serve as the draw solution with a high osmotic pressure.

According to embodiments of the disclosure, the ionic liquid used in the draw solution can be

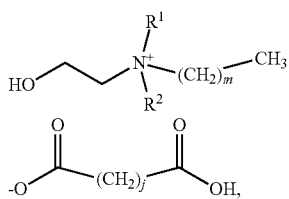

wherein m is 0, 1, or 2; $R^1$ and $R^2$ are independently methyl or ethyl; and j is 5, 6, or 7. According to embodiments of the disclosure, the ionic liquid used in the draw solution can be

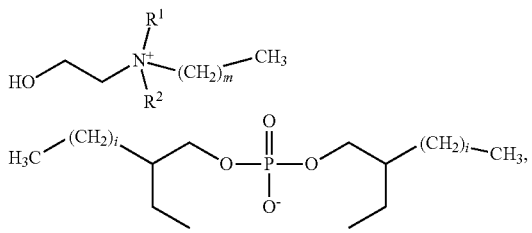

wherein m is 5, 6, or 7; $R^1$ and $R^2$ are independently methyl or ethyl; and i is independently 1, 2, or 3. According to embodiments of the disclosure, the ionic liquid used in the draw solution can be

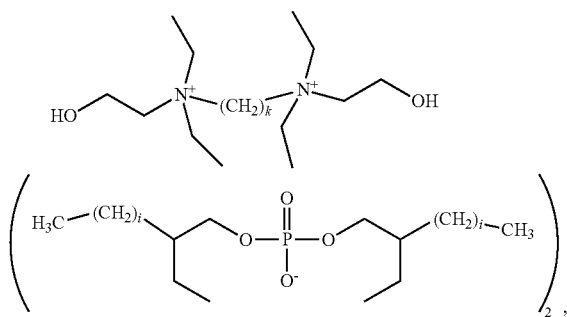

wherein k is 3, 4, 5, 6, 7, or 8; and i is independently 1, 2, or 3. Herein, the ionic liquid can be mixed with water to form a homogeneous aqueous solution at room temperature, and the aqueous solution exhibits high osmotic pressure, high conductively, and thermosensitive phase transition behavior. Therefore, the aqueous solution employing the ionic liquid is suitable to be used for preparing the draw solution of the forward osmosis process.

According to embodiments of the disclosure, the disclosure also provides a forward osmosis process, wherein the draw solution used in the forward osmosis process includes the ionic liquid of the disclosure. The forward osmosis process includes providing a forward osmosis system 100 (as shown in FIG. 1), the forward osmosis system 100 includes a semi-permeable membrane 11, wherein a draw solution tank 15 is separated from a feed water tank 13 by the semi-permeable membrane 11. Next, a brine 17 is disposed in the feed water tank 13, and a draw solution 19 is disposed in the draw solution tank 15. Since the osmotic pressure of the brine 17 is lower than the osmotic pressure of the draw solution 19, the water 21 of the brine permeates through the semi-permeable membrane into the draw solution tank 15 to mix with the draw solution 19 to form a diluted draw solution. When the water content of the diluted draw solution reaches a predetermined amount, the diluted draw solution is separated from the draw solution tank (such as a part of diluted draw solution is transformed from the draw solution tank to a treatment tank). Next, the diluted draw solution is subjected to a temperature control treatment (such as heating treatment, or cooling treatment) so that the diluted draw solution is subsequently separated into a water phase and an ionic liquid phase. According to embodiments of the disclosure, the predetermined amount of water in the diluted draw solution can be 30 wt % to 90 wt % (such as 30 wt %, 35 wt %, 40 wt %, 45 wt %, 50 wt %, 55 wt %, 60 wt %, 65 wt %, 70 wt %, 75 wt %, 80 wt %, 85 wt %, or 90 wt %).

Since the ionic liquid of the disclosure used in the draw solution is a thermoresponsive compound (thermoresponsive polymers) (i.e. the ionic liquid exhibits an upper critical solution temperature (UCST) or a lower critical solution temperature (LCST), and the ionic liquid is completely miscible with water at a temperature above (or below) the critical solution temperature). Therefore, when the temperature of the diluted draw solution is adjusted to be lower than the upper critical solution temperature (UCST) (or higher than the lower critical solution temperature (LCST)), the diluted draw solution undergoes a liquid-liquid phase separation (obtaining a water phase and an ionic liquid phase) due to an inner conformational change of the ionic liquid and the lowering affinity between water and the ionic liquid (resulting from the aggregation of the ionic liquid). As a result, the goals of recovering the draw solution and producing pure water can be achieved.

According to embodiments of the disclosure, after subjecting the diluted draw solution to the temperature control treatment (i.e. after the water phase and the ionic liquid phase in the diluted draw solution are formed), the forward osmosis process can further include introducing the ionic liquid phase into the draw solution tank to be recycled effectively, thereby achieving the goal of reusing the ionic liquid. According to embodiments of the disclosure, the method for introducing the brine into the feed water tank can be a continuous process, in order to maintain the osmotic pressure and concentration of the brine in the feed water tank 13. As a result, after the water 21 of the brine penetrates into the draw solution tank 15, the concentration and osmotic pressure of the brine 17 in the feed water tank 13 would not be increased, thereby avoiding reducing the flux of water 21 which penetrates into the draw solution tank 15. According to embodiments of the disclosure, the term "brine" of the disclosure means an alkali-metal-containing aqueous solution or an alkaline earth-metal-containing aqueous solution from industrial or natural source. For example, the brine can be waste water from a factory, a house, or a laboratory. In addition, according to embodiments of the disclosure, brine can be seawater.

According to embodiments of the disclosure, the temperature control treatment can be a cooling treatment. Namely, during the temperature control treatment, the temperature of the diluted draw solution can be reduced to below room temperature, thereby forcing the diluted draw solution to undergo a phase separation. Herein, the ionic liquid used in the draw solution can be an ionic liquid exhibiting upper critical solution temperature (UCST), such as

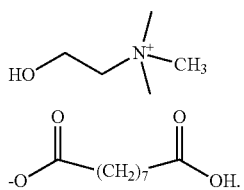

Herein, the aqueous solution including the ionic liquid exhibits an upper critical solution temperature (UCST) below 10° C.-35° C.

According to embodiments of the disclosure, the temperature control treatment can be a heating treatment. Namely, during the temperature control treatment, the temperature of the diluted draw solution can be increased to above room temperature, thereby forcing the diluted draw solution to undergo a phase separation. Herein, the ionic liquid used in the draw solution is

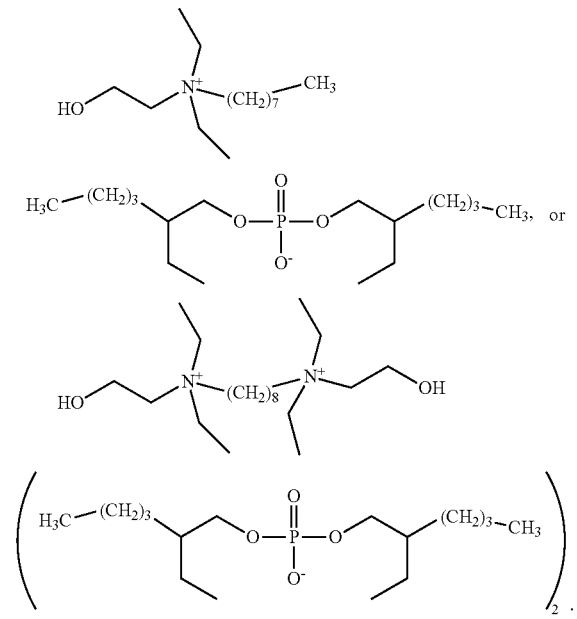

In addition, the aqueous solution including the ionic liquid exhibits a lower critical solution temperature (LCST) above 43° C.-60° C. when ionic liquid is

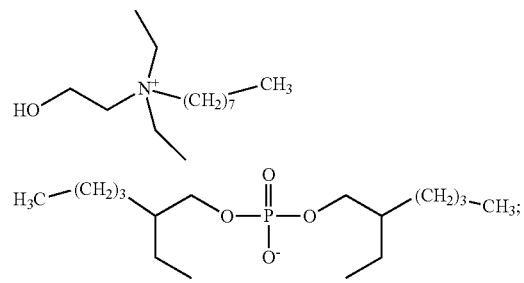

and the aqueous solution including the ionic liquid exhibits a lower critical solution temperature (LCST) above 65° C.-75° C. when the ionic liquid is

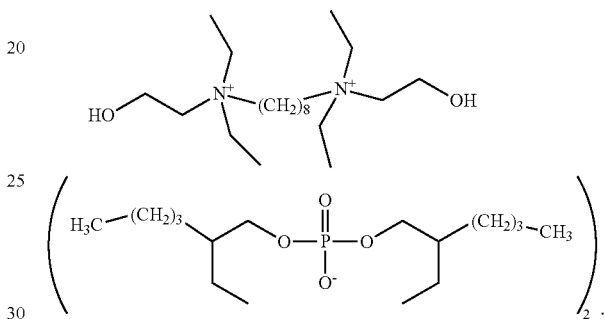

According to embodiments of the disclosure, due to the use of the draw solution including the ionic liquid of the disclosure, the forward osmosis process of the disclosure can have advantages of high flux, low power consumption, low membrane fouling, and low back diffusion of solute. As a result, the stability of desalination of the forward osmosis process of the disclosure can be increased and the cost of the forward osmosis process of the disclosure can be reduced.

Below, exemplary embodiments will be described in detail with reference to the accompanying drawings so as to be easily realized by a person having ordinary knowledge in the art. The inventive concept may be embodied in various forms without being limited to the exemplary embodiments set forth herein. Descriptions of well-known parts are omitted for clarity, and like reference numerals refer to like elements throughout.

EXAMPLES

Example 1

First, (2-hydroxyethyl) octyldiethylammonium bromide (with a structure of

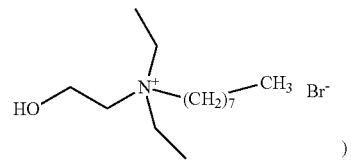

(hereafter referred to as [Ch228][Br]) was prepared with following steps. 52 g of (2-hydroxyethyl)diethylamine (0.44 mole), 85 g of (1-octylbromide) (0.44 mole), and 150 ml of acetonitrile were added into a reaction bottle, and the result was stirred at 80° C. for 24 hours. After cooling to room temperature, the result was dropwisely added into 1.5 L of diethyl ether, white precipitate was formed. After filtration, the obtained filter cake was dried, (2-hydroxyethyl) octyldiethyl ammonium bromide ([Ch228][Br]) was obtained.

Next, (2-hydroxyethyl)octyldiethyl ammonium hydroxide (with a structure of

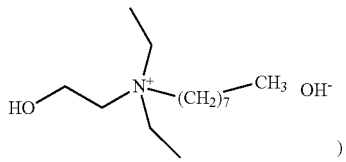

)

(hereafter referred to as [Ch228][OH]) was prepared from [Ch228][Br] by means of an ion exchange resin. Next, 82.8 g of [Ch228][OH] (0.335 mol), 108 g of di(2-ethylhexyl) phosphate (0.335 mmol) and 500 ml of water/ethanol solution (the volume ratio of water to ethanol is 1:1) were added into a reaction bottle, the result was stirred at room temperature for 12 hours. Next, the result was extracted with 200 ml of dichloromethane, and then the organic phase was collected. After dehydration and concentration, Ionic liquid (I) (with a structure of

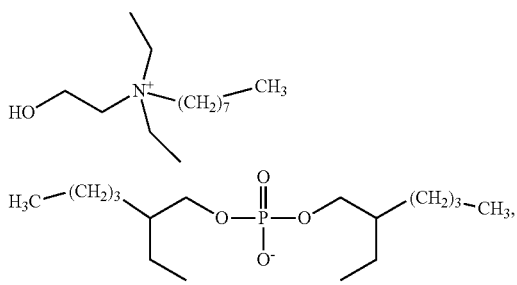

hereafter referred to as [Ch228][DEHP]) was obtained. The measurement results of nuclear magnetic resonance spectrometry of [Ch228][DEHP] are shown below: $^1$H-NMR (500 MHz in $D_2O$): 0.71~0.82 (m, 9H, $CH_3$—), 1.09~1.29 (m, 26H, —$CH_2$—), 1.31 (m, 2H, —CH—), 1.52 (br, 2H, $N^+CH_2CH_2$—), 3.09 (br, 2H, $N^+CH_2CH_2$—), 3.23 (m, 6H, $N^+CH_2$), 3.46 (t, 4H, —$OCH_2$), 3.85 (t, 2H, —$CH_2OH$).

Figure 2:
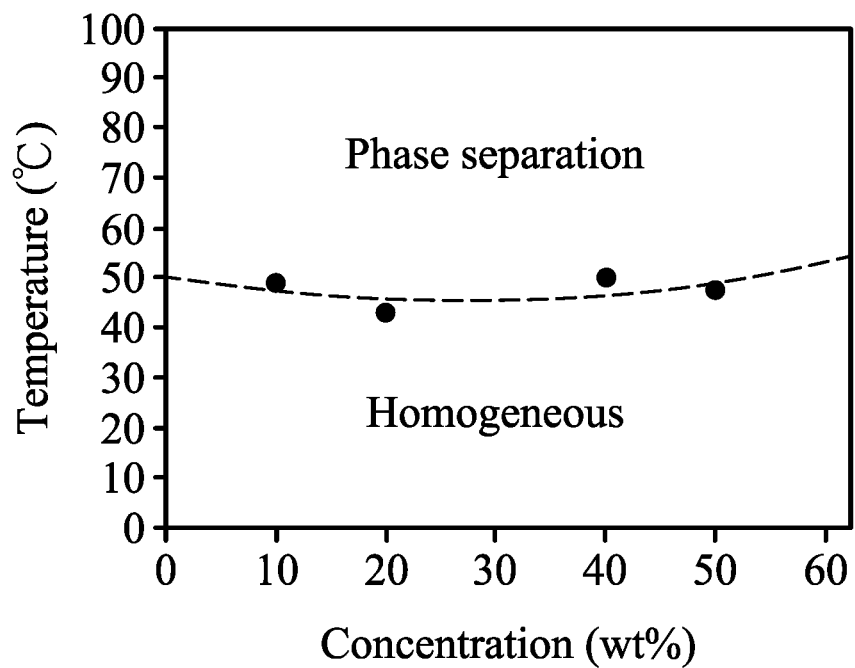
FIG. 2 is a graph plotting the phase separation temperature of the aqueous solution as disclosed in Example 1 (having the ionic liquid) against the concentration of the ionic liquid.

The ionic liquid [Ch228][DEHP] was mixed with water under various weight ratio, and the obtained mixtures were stood at room temperature for a period of time. The results were observed to determine whether a phase separation was induced, and the critical solution temperature thereof was recorded. The results are shown in FIG. 2. According to the results, the ionic liquid [Ch228][DEHP] is an ionic liquid which exhibits lower critical solution temperature (LCST). As shown in FIG. 2, when the amount of ionic liquid [Ch228][DEHP] is between 10 wt % and 50 wt % (based on the weight of the aqueous solution), the aqueous solution exhibits a lower critical solution temperature (LCST) above 43° C.-60° C. Herein, a phase separation (i.e. liquid-liquid phase separation) of water to the ionic liquid was observed.

The osmotic pressure of the aqueous solutions with various concentration of ionic liquid were measured by an osmometer (OSMOMAT 030; GONOTEC), and the results are shown in Table 1. The osmotic pressure of the aqueous solution was measured by freezing point depression method. The principle of the freezing point depression method is measuring the freezing point of a solution of the ionic liquid. If one mole of a solute (e.g. ionic liquid) could lower the freezing point of one kilogram of water (containing the solute) by 1.86° C., the osmotic pressure of the solute can be defined as 1 Osmol/kg. As shown in Table 1, when the aqueous solution has a concentration of the ionic liquid [Ch228][DEHP] of 30 wt %, the osmotic pressure can be about 0.9 Osmol/kg. In addition, the aqueous solution, which has a high concentration of the ionic liquid [Ch228][DEHP], has an osmotic pressure that exceeds the detectable range of the instrument. Therefore, the osmotic pressure of the aqueous solution, which has a concentration of the ionic liquid [Ch228][DEHP] of 40 wt %, can be estimated according to an equation determined by the osmotic pressure of the aqueous solutions having the concentration of the ionic liquid [Ch228][DEHP] between 20 wt % and 30 wt %. The results are shown in Table 1. The experimental results show that the osmotic pressure of the aqueous solution having a concentration of the ionic liquid [Ch228][DEHP] of 40 wt % is greater than the osmotic pressure of seawater. Therefore, the aqueous solution including the ionic liquid of the disclosure can serve as the draw solution used in the seawater desalination process.

TABLE 1

| | concentration of [Ch228] [DEHP] | | |
| --- | --- | --- | --- |
| | 20% | 25 wt % | 30 wt % |
| osmotic pressure (Osmol/kg) | 0.279 | 0.502 | 0.882 |

*The osmotic pressure of seawater (0.6M NaCl) is 1.2 Osmol/kg

Figure 3:
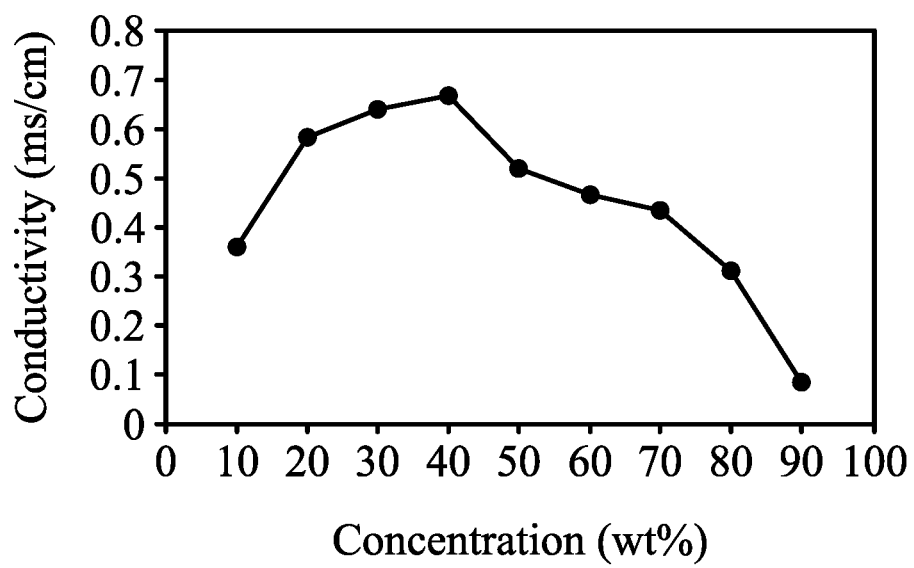
FIG. 3 is a graph plotting the conductivity of the aqueous solution as disclosed in Example 1 (having the ionic liquid) against the concentration of the ionic liquid.

FIG. 3 is a graph plotting the conductivity against the concentration of the ionic liquid [Ch228][DEHP]. As shown in FIG. 3, the initial conductivity of the aqueous solution having a high concentration of the ionic liquid [Ch228][DEHP] is about 0.1 mS/cm. The conductivity, however, is increased with respect to the water content of the aqueous solution. Since the ionic liquid-rich phase is modeled as an ion-pair, the self-aggregation of the ionic liquid in the aqueous solution would be reduced with respect to the increase of water content, resulting in that the ionic liquid dissociates into an anion and a cation. Due to these characteristics of ionic liquid, the forward osmosis process of the disclosure can be performed stably and the water flux of the forward osmosis process can be increased effectively.

Figure 4:
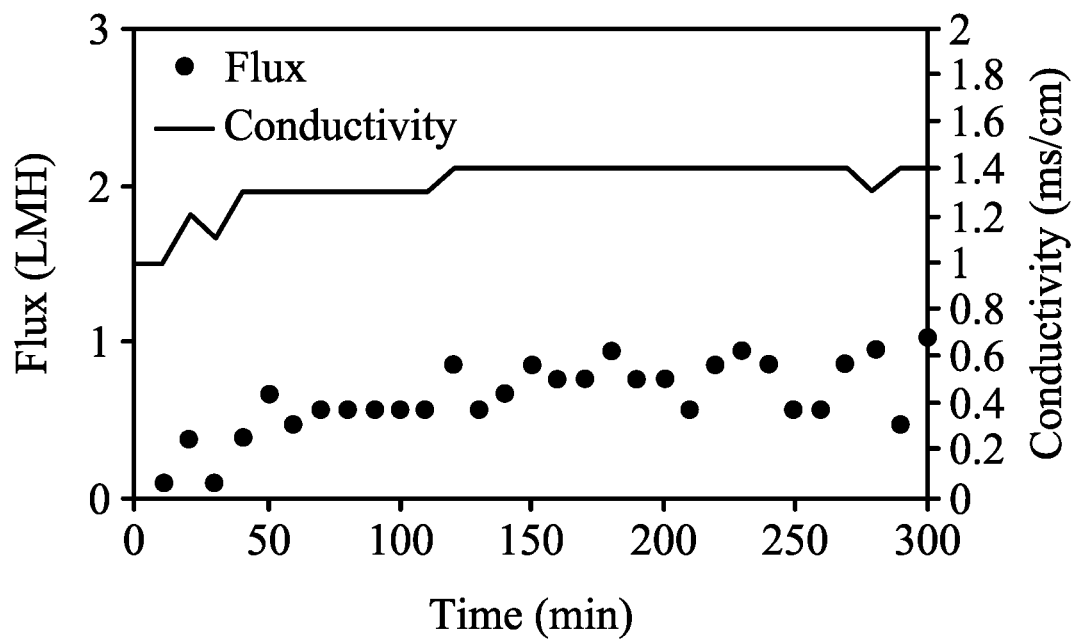
FIG. 4 is a graph plotting the weight changes (water flux) between the feed water tank and the draw solution tank against time, and the conductivity of the draw solution tank (including ionic liquid of Example 1) against time.

A forward osmosis device assembled in the laboratory was provided, wherein the forward osmosis module was plate type, the flow channel design was dual-channel circulation type, and the membrane (commercially available from Dow FilmTec Company with a trade number of TW30-1812) (with an effective area of 64 cm$^2$) was served as the semi-permeable membrane. Solutions were respectively introduced into the feed water tank and the draw solution tank by a pump. The weight of the feed water tank and the weight of the draw solution tank at different points in time were measured under a scan rate of 25 cm/s and recorded. The water flux was calculated via the weight change, the film area, and the experiment period, as shown in FIG. 4. The ionic liquid [Ch228][DEHP] was introduced into the draw solution tank and de-ionized water was introduced into the feed water tank. In an initial stage, the conductivity of the mixture liquid in the draw solution tank and the water flux were increased with respect to the increase of the experiment period. After being stably operated for 5 hours, the water flux of the solution in the draw solution tank was still maintained (the average flux was 0.64 LMH).

Example 2

First, 1,8-octanediyl-bis((2-hydroxyethyl)diethylammonium) dibromide, (with a structure of

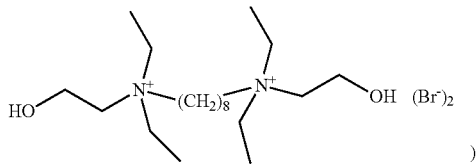

) (hereafter referred to as [DCh8-22][Br$_2$]) was prepared with following steps. 52 g of (2-hydroxyethyl) diethylamine (0.44 mole), 60 g of 1,8-dibromooctane (0.22 mole), and 100 ml of acetonitrile were added into a reaction bottle, and the result was stirred at 80° C. for 24 hours. After cooling to room temperature, the result was dropwisely added into 1.5 L of diethyl ether, white precipitate was formed. After filtration, the obtained filter cake was dried, obtaining 1,8-octanediyl-bis ((2-hydroxyethyl) diethylammonium bromide ([DCh8-22][Br$_2$]).

Next, (2-hydroxyethyl)octyldiethyl ammonium hydroxide (with a structure of

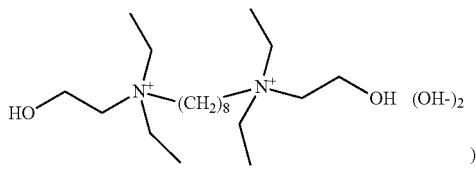

) (hereafter referred to as [DCh8-22][OH$_2$]) was prepared from 1,8-octanediyl-bis ((2-hydroxyethyl) diethylammonium bromide ([DCh8-22][Br$_2$]) by means of an ion exchange resin. Next, 45.25 g of [DCh8-22][OH$_2$] (0.15 mol), 96.73 g of di(2-ethylhexyl) phosphate (0.3 mmol) and 500 ml of water/ethanol solution (the volume ratio of water to ethanol is 1:1) were added into a reaction bottle, the result was stirred at room temperature for 12 hours. Next, the result was extracted with 200 ml of dichloromethane, and then the organic phase was collected. After dehydration and concentration, Ionic liquid (II) (with a structure of

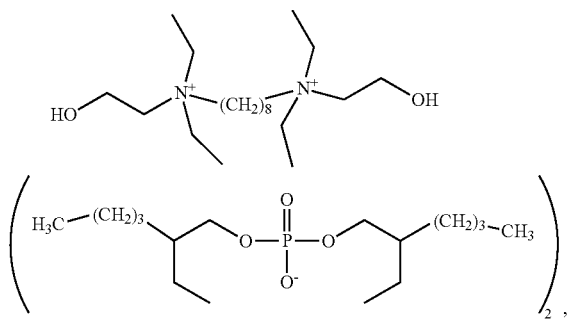

hereafter referred to as [DCh8-22][DEHP]). The measurement result of nuclear magnetic resonance spectrometry of [DCh8-22][DEHP] are shown below: $^1$H-NMR (500 MHz in D$_2$O): 0.71~0.80 (m, 24H, CH$_3$—), 1.09~1.29 (m, 24H, —CH$_2$—), 1.36 (m, 4H, —CH—), 1.54 (br, 4H, N$^+$CH$_2$CH$_2$—), 3.50 (br, 4H, N$^+$CH$_2$CH$_2$—), 3.31 (m, 12H, N$^+$CH$_2$—), 3.55 (dd, 4H, —OCH$_2$), 3.85 (t, 4H, —CH$_2$OH).

The ionic liquid [DCh8-22][DEHP] was mixed with water under various weight ratio, and the obtained mixtures were stood at room temperature for a period of time. The results were observed to determine whether a phase separation was induced, and the critical solution temperature thereof was recorded. The results are shown in Table 2. According to the results, the ionic liquid [DCh8-22][DEHP] is an ionic liquid which exhibits lower critical solution temperature (LCST). When the amount of ionic liquid [DCh8-22][DEHP] is between 10 wt % and 30 wt % (based on the weight of the aqueous solution), the aqueous solution exhibits a lower critical solution temperature (LCST) above 67° C.-74° C. Herein, a phase separation (i.e. liquid-liquid phase separation) of water to the ionic liquid was observed.

TABLE 2

| | concentration of [DCh8-22][DEHP] | | |
|---|---|---|---|
| | 10 wt % | 20 wt % | 30 wt % |
| critical solution temperature | 71° C. | 67° C. | 74° C. |

Example 3

100 g of choline hydroxide aqueous solution (46 wt %, 0.38 mole of choline hydroxide dissolved in water) was added into a reaction bottle. Next, 74.42 g of nonanedioic acid was dropwisely added into the reaction bottle. After reacting at room temperature for 24 hours, the result was extracted with 200 ml of dichloromethane, and then the organic phase was collected. After dehydration and concentration, Ionic liquid (III) (with a structure of

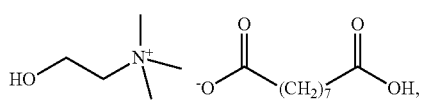

hereafter referred to as [Ch][Aze]) was obtained. The measurement results of nuclear magnetic resonance spectrometry of [Ch][Aze] are shown below: $^1$H-NMR (500 MHz in D$_2$O): 1.17 (m, 6H, —CH$_2$—), 1.41 (m, 4H, —CH$_2$—), 2.10 (t, 4H, —OOCCH$_2$—), 3.03 (s, 9H, N$^+$CH$_3$), 3.35 (t, 2H, N$^+$CH$_2$CH$_2$—), 3.90 (m, 2H, —CH$_2$OH).

Figure 5:
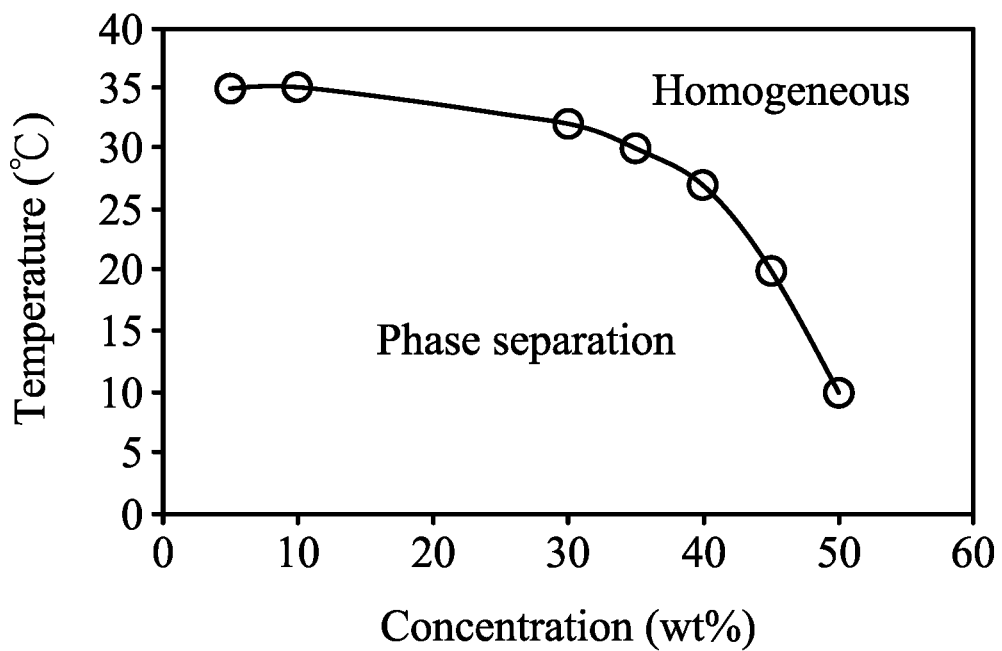
FIG. 5 is a graph plotting the phase separation temperature of the aqueous solution as disclosed in Example 3 (having the ionic liquid) against the concentration of the ionic liquid.

The ionic liquid [Ch][Aze] was mixed with water under various weight ratio, and the obtained mixtures were stood at room temperature for a period of time. The results were observed to determine whether a phase separation was induced, and the critical solution temperature thereof was recorded. The results are shown in FIG. 5. According to the results, the ionic liquid [Ch][Aze] is an ionic liquid which exhibits upper critical solution temperature (UCST). As shown in FIG. 5, when the amount of ionic liquid [Ch228][DEHP] is between 5 wt % and 50 wt % (based on the weight of the aqueous solution), the aqueous solution exhibits an upper critical solution temperature (UCST) below 10° C.-35° C. Herein, a phase separation (i.e. liquid-liquid phase separation) of water to the ionic liquid was observed.

The osmotic pressure of the aqueous solution with various concentration of ionic liquid was measured by a osmometer (OSMOMAT 030; GONOTEC), and the results are shown in Table 3.

TABLE 3

| | [Ch][Aze] concentration | | | | |
|---|---|---|---|---|---|
| | 30 wt % | 40 wt % | 50 wt % | 60 wt % | 70 wt % |
| osmotic pressure (Osmol/kg) | 2.7 | 4.2 | 6.2 | 9.4 | 14.5 |

*seawater osmotic pressure (0.6M NaCl) is 1.2 Osmol/kg

As shown in Table 3, when the aqueous solution has the concentration of the ionic liquid [Ch][Aze] between 30 wt % and 70 wt %, the osmotic pressure of the aqueous solution is 2-15 times the osmotic pressure of seawater. Therefore, the aqueous solution including the ionic liquid [Ch][Aze] exhibits high osmotic pressure, and is suitable to serve as a forward osmosis draw solution.

Figure 6:
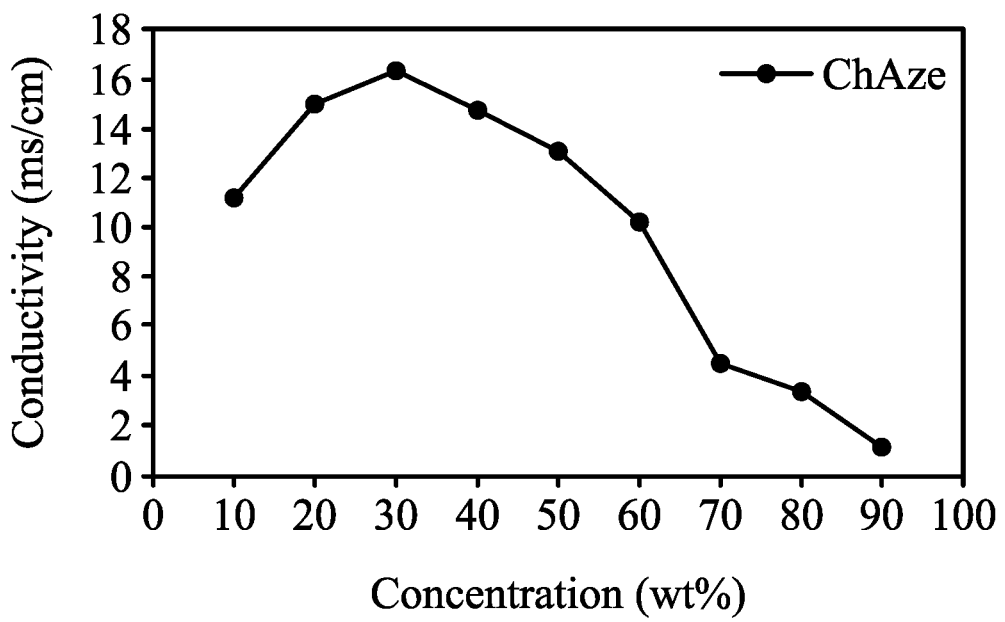
FIG. 6 is a graph plotting the conductivity of the aqueous solution as disclosed in Example 3 (having the ionic liquid) against the concentration of the ionic liquid.

FIG. 6 is a graph plotting the conductivity against the concentration of the ionic liquid [Ch][Aze]. As shown in FIG. 6, the initial conductivity of the aqueous solution having a high concentration of the ionic liquid [Ch][Aze] is about 1.1 mS/cm. The conductivity, however, is increased with respect to the water content of the aqueous solution. Since the ionic liquid-rich phase is modeled as an ion-pair, the self-aggregation of the ionic liquid in the aqueous solution would be reduced with respect to the increase of water content, resulting in that the ionic liquid dissociates into an anion and a cation. Due to these characteristics of the ionic liquid, the forward osmosis process of the disclosure can be performed stably and the water flux of the forward osmosis process can be effectively increased.

Figure 7:
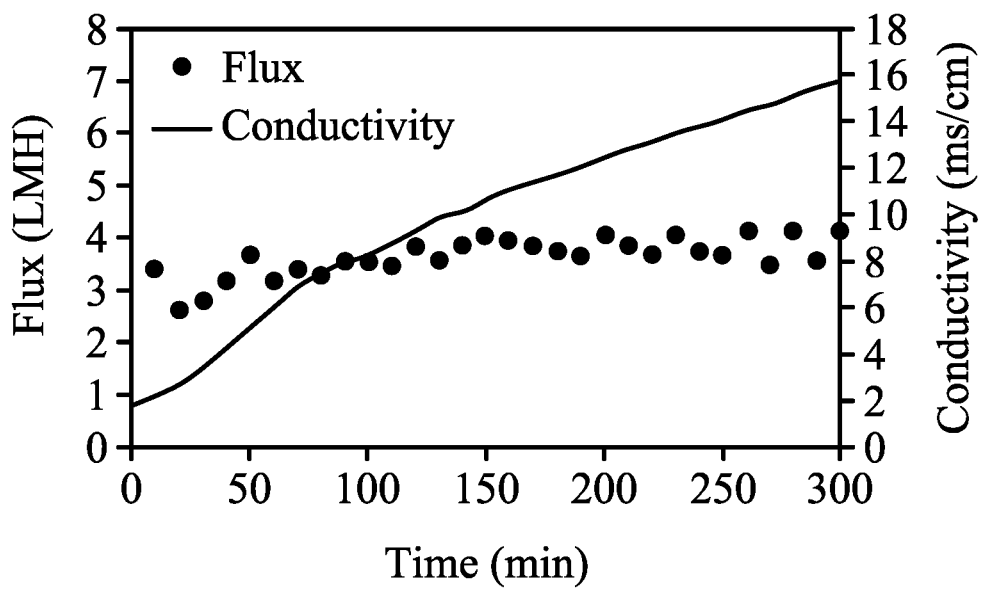
FIG. 7 is a graph plotting the weight changes (water flux) between the feed water tank and the draw solution tank against time, and the conductivity of the draw solution tank (having ionic liquid of Example 3) against time.

A forward osmosis device assembled in the laboratory was provided, wherein the forward osmosis module was plate type, the flow channel design was dual-channel circulation type, and the membrane (commercially available from Dow FilmTec Company with a trade number of TW30-1812) (with an effective area of 64 cm²) was served as the semi-permeable membrane. Solutions were respectively introduced into the feed water tank and the draw solution tank by a pump. The weight of the feed water tank and the weight of the draw solution tank at different points in time were measured under a scan rate of 25 cm/s and recorded. The water flux was calculated via the weight change, the film area, and the experiment period, as shown in FIG. 7. The ionic liquid [Ch][Aze] was introduced into the draw solution tank and de-ionized water was introduced into the feed water tank. In an initial stage, the conductivity of the mixture liquid in the draw solution tank and the water flux were increased with respect to the increase of the experiment period. After being stably operated for 5 hours, the water flux of the solution in the draw solution tank was still maintained (the average flux was above 3 LMH).

It will be clear that various modifications and variations can be made to the disclosed methods and materials. It is intended that the specification and examples be considered as exemplary only, with the true scope of the disclosure being indicated by the following claims and their equivalents.

What is claimed is:

1. An ionic liquid, having a structure represented by Formula (I):

$$AB_n \quad \text{Formula (I)},$$

wherein A is

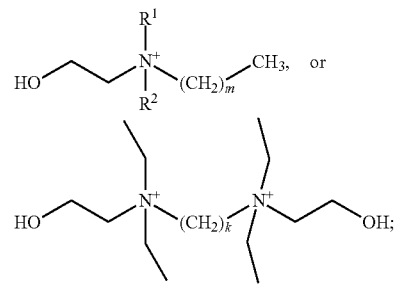

$n$ is 1 or 2; $m$ is 0, or an integer from 1 to 7; $R^1$ and $R^2$ are independently methyl or ethyl; $k$ is an integer from 3 to 8; B is

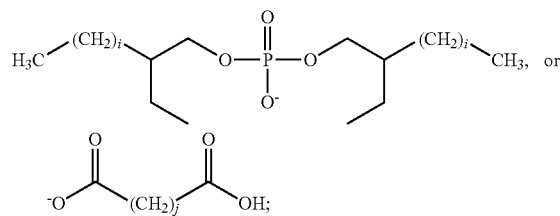

$i$ is independently 1, 2, or 3; and $j$ is 5, 6, or 7.

2. The ionic liquid as claimed in claim 1, wherein $n=1$; A is

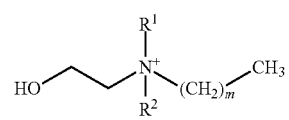

$m$ is 0, 1, or 2; $R^1$ and $R^2$ are independently methyl or ethyl; B is

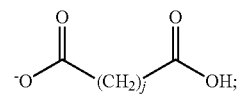

and $j$ is an integer from 5 to 7.

3. The ionic liquid as claimed in claim 2, wherein A is

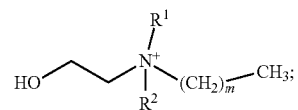

$n$ is 1; $m$ is 0; $R^1$ and $R^2$ are methyl; B is

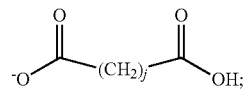

and j is 7.

4. The ionic liquid as claimed in claim 1, wherein n=1; A is

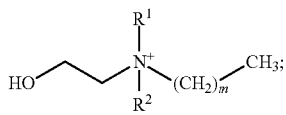

m is 5, 6, or 7; $R^1$ and $R^2$ are independently methyl or ethyl; B is

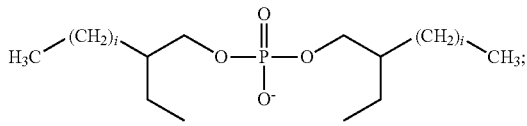

and i is independently 1, 2, or 3.

5. The ionic liquid as claimed in claim 4, wherein A is

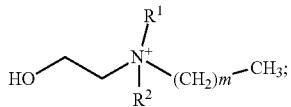

n is 1; m is 7; $R^1$ and $R^2$ are ethyl; B is

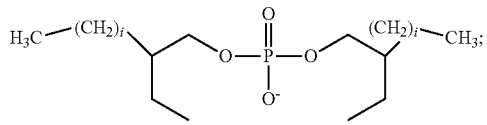

and i is 3.

6. The ionic liquid as claimed in claim 1, wherein n=2; A is

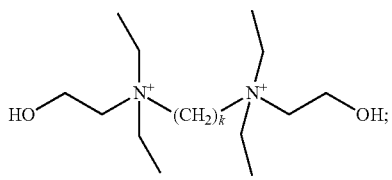

k is an integer from 3 to 8; B is

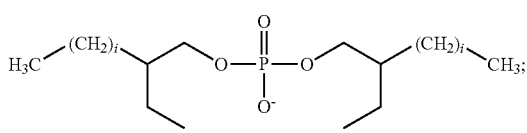

and i is independently 1, 2, or 3.

7. The ionic liquid as claimed in claim 1, wherein A is

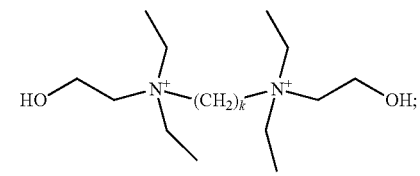

k is 8; n is 2; B is

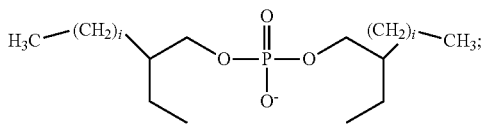

and i is 3.

8. A forward osmosis process, comprising:
providing a semi-permeable membrane, wherein a draw solution tank is separated from a feed water tank by the semi-permeable membrane;
introducing a draw solution into the draw solution tank, wherein the draw solution comprises the ionic liquid as claimed in claim 1;
introducing brine into the feed water tank, wherein an osmotic pressure of the brine is lower than an osmotic pressure of the ionic liquid so that water of the brine permeates through the semi-permeable membrane into the draw solution to obtain a diluted draw solution;
extracting the diluted draw solution from the draw solution tank; and
subjecting the diluted draw solution to a temperature control treatment so that the diluted draw solution is subsequently separated into a water phase and an ionic liquid phase.

9. The forward osmosis process as claimed in claim 8, wherein the draw solution comprises water and the ionic liquid as claimed in claim 1.

10. The forward osmosis process as claimed in claim 9, wherein the amount of ionic liquid is 10 wt % to 70 wt %, based on the weight of the draw solution.

11. The forward osmosis process as claimed in claim 8, wherein the temperature control treatment is a cooling treatment.

12. The forward osmosis process as claimed in claim 11, wherein A is

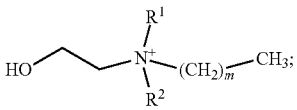

n is 1; m is 0; $R^1$ and $R^2$ are methyl; B is

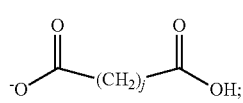

j is 7.

13. The forward osmosis process as claimed in claim 12, wherein the diluted draw solution exhibits an upper critical solution temperature (UCST) phase separation below 10° C.-35° C.

14. The forward osmosis process as claimed in claim 8, wherein the temperature control treatment is a heating treatment.

15. The forward osmosis process as claimed in claim 14, wherein A is

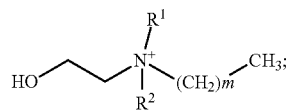

n is 1; m is 7; $R^1$ and $R^2$ are ethyl; B is

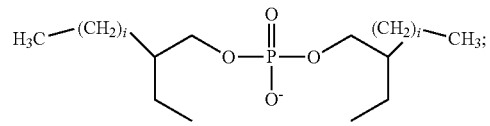

and i is 3.

16. The forward osmosis process as claimed in claim 15, wherein the diluted draw solution exhibits a lower critical solution temperature (LCST) phase separation above 43° C.-60° C.

17. The forward osmosis process as claimed in claim 15, further comprising, after subjecting the diluted draw solution to the temperature control treatment, introducing the ionic liquid phase into the draw solution tank.

18. The forward osmosis process as claimed in claim 14, wherein A is

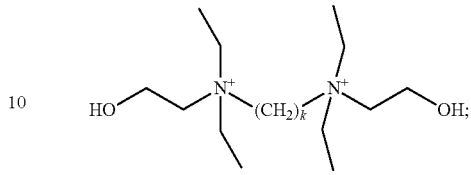

k is 8; n is 2; B is

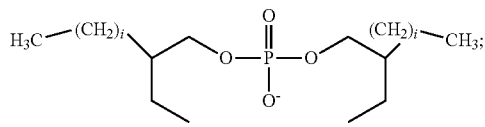

and i is 3.

19. The forward osmosis process as claimed in claim 18, wherein the diluted draw solution exhibits a lower critical solution temperature (LCST) phase separation above 65° C.-75° C.

* * * * *